United States Patent [19]

Connor et al.

[11] Patent Number: 5,194,639

[45] Date of Patent: Mar. 16, 1993

[54] PREPARATION OF POLYHYDROXY FATTY ACID AMIDES IN THE PRESENCE OF SOLVENTS

[75] Inventors: Daniel S. Connor; Jeffrey J. Scheibel; Roland G. Severson, all of Cincinnati, Ohio

[73] Assignee: The Procter & Gamble Company, Cincinnati, Ohio

[21] Appl. No.: 756,093

[22] Filed: Sep. 6, 1991

Related U.S. Application Data

[63] Continuation-in-part of Ser. No. 590,391, Sep. 28, 1990.

[51] Int. Cl.⁵ .................... C07C 231/02; C11C 3/00
[52] U.S. Cl. .................................................. 554/66
[58] Field of Search ......................... 260/404; 554/66

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,653,932 | 9/1953 | Schwartz | 260/211 |
| 2,662,073 | 12/1953 | Mehltretter et al. | 260/102 |
| 2,703,798 | 3/1955 | Schwartz | 260/211 |
| 2,844,609 | 7/1958 | Tesoro | 260/404 |
| 2,891,052 | 6/1959 | Boettner et al. | 260/211 |
| 2,954,347 | 9/1960 | St. John et al. | 252/109 |
| 2,991,296 | 7/1961 | Scherr | 260/404 |
| 2,993,887 | 7/1961 | Zech | 260/211 |
| 3,257,436 | 6/1966 | Lindner | 260/404 |
| 3,285,856 | 11/1966 | Lew | 252/152 |
| 3,576,749 | 4/1971 | Megson et al. | 252/132 |
| 3,637,495 | 1/1972 | Eckert et al. | 252/8.8 |
| 3,704,228 | 11/1972 | Eckert | 252/117 |
| 3,920,586 | 11/1975 | Bonaparte et al. | 252/531 |
| 3,929,679 | 12/1975 | Laughlin et al. | 252/526 |
| 3,985,669 | 10/1976 | Krummel et al. | 252/116 |
| 3,988,255 | 10/1976 | Seiden | 252/107 |
| 4,094,808 | 6/1978 | Stewart et al. | 252/186 |
| 4,129,511 | 12/1978 | Ogoshi et al. | 252/140 |
| 4,223,163 | 9/1980 | Guilloty | 568/618 |
| 4,292,212 | 9/1981 | Melby | 252/547 |
| 4,483,781 | 11/1984 | Hartman | 252/174.12 |
| 4,540,821 | 9/1985 | Larkin et al. | 564/473 |
| 4,565,647 | 1/1986 | Llenado | 252/354 |
| 4,664,839 | 5/1987 | Rieck | 252/175 |
| 4,704,224 | 11/1987 | Saud | 252/132 |
| 4,843,154 | 6/1989 | Klein et al. | 536/4.1 |
| 5,009,814 | 4/1991 | Kelkenberg et al. | 252/528 |

FOREIGN PATENT DOCUMENTS

| | | |
|---|---|---|
| 206283 | 2/1957 | Australia . |
| 220676 | 5/1987 | European Pat. Off. . |
| 255033 | 7/1987 | European Pat. Off. . |
| 0285768 | 2/1988 | European Pat. Off. ............ 260/404 |
| 282816 | 9/1988 | European Pat. Off. . |
| 422508 | 4/1991 | European Pat. Off. . |
| 2038103 | 2/1972 | Fed. Rep. of Germany . |
| 2226872 | 12/1973 | Fed. Rep. of Germany . |
| 2404070 | 8/1975 | Fed. Rep. of Germany . |
| 1580491 | 9/1969 | France . |
| 2657611 | 2/1991 | France . |
| 3-112904-A | 5/1991 | Japan . |
| 8304412 | 12/1983 | PCT Int'l Appl. . |
| 420518 | 11/1934 | United Kingdom . |
| 519381 | 3/1940 | United Kingdom . |
| 771423 | 4/1957 | United Kingdom . |
| 809060 | 2/1959 | United Kingdom . |
| 2242686 | 9/1991 | United Kingdom . |

OTHER PUBLICATIONS

Synthesis of Long Chain N-Alkyllactylamines from Unprotected Lactose—A new Series of Non-Ionic Surfactants, Latge et al. J. Dispersion Science and Technology, 12(3&4), pp. 227-237 (1991).

"N-D-Gluco-N-methylalkanamide Compounds, a New Class of Non-Ionic Detergents For Membrane Biochemistry", Biochem. J. (1982), vol. 207, pp. 363-366, Hildreth.

H. Kelkenberg, Tenside Surfactants Detergents 25 (1988) pp.8-13.

Relative Stabilities of d-Glucose-Amine Derivatives, Mohammad and Olcott, JACS, Apr. 1947, p. 969.

[23] 1-Amino-1-deoxy-D-glucitol, Long and Bollenback, Meth. Carbohyd. Chem., vol. 2, (1963), pp. 79-83.

The Reaction of Glucose with Some Amines, Mitts and Hixon, JACS, vol. 66, (1944), pp. 483-486.

Synthesis of ¹⁴C-Labeled N-Methylglucamine, Heeg et al., Can. J. of Pharmaceutical Sciences, vol. 10, No. 3 (1975), pp. 75-76.

Primary Examiner—José G. Dees
Assistant Examiner—Barbara S. Frazier
Attorney, Agent, or Firm—Jerry J. Yetter; Rose Ann Dabek

[57] ABSTRACT

Polyhydroxy fatty acid amide materials are prepared from reactants such as N-methylglucamine and fatty acid esters in the presence of hydroxy solvents. Polyhydroxy fatty acid amide detersive surfactants are secured. By-product and color formation are minimized.

6 Claims, No Drawings

PREPARATION OF POLYHYDROXY FATTY ACID AMIDES IN THE PRESENCE OF SOLVENTS

CROSS REFERENCE TO RELATED APPLICATION

This application is a continuation-in-part of co-pending application Ser. No. 590,391 filed Sep. 28, 1990.

FIELD OF THE INVENTION

The present invention relates to a process for preparing polyhydroxy fatty acid amide materials which can be used as surfactants, and the like.

BACKGROUND OF THE INVENTION

A wide variety of nonionic surfactants are available to detergent formulators for use in detergent compositions of various types. Included among such materials are the ethylene oxide derivatives of fatty alcohols (nonionic surfactants), and many such materials are used in modern laundry detergent compositions. However, there is a continuing search for high performance detersive surfactants and various alternatives to the ethoxylated alcohols have been suggested. Nonetheless, a review of current commercial laundry detergent formulations would indicate that, although many nonionic surfactants have been suggested for detergency use, the ethoxylated alcohols (and in some instances, ethoxylated alkyl phenols) are the only nonionics in common usage.

One class of nonionic detersive surfactants disclosed in the literature comprises the polyhydroxy fatty acid amides. These materials are taught to be mild, high sudsing surfactants. Accordingly, one might have expected that these materials would have found wide usage in detergent formulations; however, that does not appear to be the case. It might be suggested that one reason polyhydroxy fatty acid amides have not come into widespread use is their difficulty of manufacture.

It has now been determined that polyhydroxy fatty acid amide surfactants can be prepared by a rapid, low temperature process which exhibits high conversion rates and which yields products that are low in undesirable color bodies. Moreover, it has now bee determined that polyhydroxy fatty acid amides can be prepared with low by-product formation, with considerable flexibility of reactants and with maximum re-use of reactants with minimal waste and limited re-cycle.

BACKGROUND ART

A number of years ago, processes were explored for making textile assistants or detergents from fatty acids or their derivatives in combination with N-alkylglucamines, the latter made by reductive amination of glucose. Glucose reductive amination processes are more fully disclosed in U.S. Pat. No. 2,016,962, Flint et al, issued Oct. 8, 1935.

U.S. Pat. No. 1,985,424, Piggott, issued Dec. 25, 1934 discloses manufacturing "textile assistants" by reacting (a) the product of heating glucose and aqueous methylamine in presence of hydrogen and a hydrogenating catalyst under pressure with (b) an organic carboxylic acid such as stearic acid or oleic acid. The condensation product, prepared at about 160° C., is said to be "predominantly, if not exclusively, an amide" and is assertedly of the formula $R-CO-NR_1-CH_2-(CHOH)_4-CH_2OH$ wherein R is an alkyl radical containing at least 3 carbon atoms, while $R_1$ is hydrogen or an alkyl radical.

U.S. Pat. No. 2,703,798, Schwartz, issued Mar. 8, 1955 asserts that compositions produced by reacting fatty acids or acid anhydrides with N-alkylglucamines (presumably such as the process as taught by Piggott) have poor color and poor detergency properties. It is indeed chemically reasonable that more than one compound can be formed by the Piggott process. Piggott makes no attempt to quantitatively prove the structures of the compounds or mixtures he prepared.

Schwartz ('798) goes on to report an improvement as a result of reacting fatty ester (as distinct from fatty acid or anhydride) with N-alkylglucamines. Although this process may overcome one or another deficiency of the art, such as of Piggott, it now transpires that the Schwartz process still has difficulties, in particular, in that complex mixtures of compounds can be formed even by the Schwartz process. The reaction may take several hours and the process can fail to give high quality product. Neither the process of Piggott not the process of Schwartz is known to have ever borne fruit in commercial practice.

In more detail, Schwartz notes that only one of several possible chemical reactions takes place when N-monoalkylglucamines are condensed with fatty esters or oils. The reaction is said to give compounds formulated as amides, e.g.,

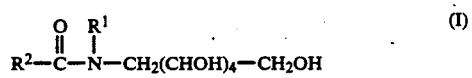

where $R^2$ is fatty alkyl and $R^1$ is a short-chain alkyl, typically methyl. This structure is apparently the same as the structure proposed by Piggott. Schwartz contrasts the single-product outcome he believes he secures with compounds he asserts are actually produced when acids are reacted with N-alkylglucamines, namely mixtures of the amide (I) with one or more by-products, to which he assigns esteramide and esteramine structures and which assertedly include compounds which are "inert and waxy, impairing the surface activity of" the structure (I) amide.

According to Schwartz, approximately equimolar proportions of N-monoalkylglucamines can be reacted with fatty alkyl esters by heating at 140° C.–230° C., preferably 160° C.–180° C. at normal, reduced or superatmospheric pressures for a period "somewhat in excess of one hour" during which time two initially immiscible phases merge to form a product said to be a useful detergent.

Suitable N-monoalkylglucamines are illustrated by N-methylglucamine, N-ethylglucamine, N-isopropylglucamine and N-butylglucamine. Suitable fatty alkyl esters are illustrated by the product of reacting a $C_6$–$C_{30}$ fatty acid with an aliphatic alcohol e.g., methyl ester of lauric acid. Mixed glycerides of Manila oil or mixed glycerides of cochin coconut oil can apparently also be used as the fatty ester. When the glucamine is N-methylglucamine, the corresponding products with these fatty esters are characterized as the "fatty acid amides of N-methylglucamine", which are useful detergent surfactants. Another specific composition reported is assertedly "N-isopropylglucamine coconut fatty acid amide".

U.S. Pat. No. 2,993,887, Zech, issued Jul. 25, 1961 reveals there is even more complexity to the reactions of fatty substances with N-methylglucamine. In particular, Zech asserts that the products of high-temperature reaction (180° C.-200° C.) within the range disclosed by Schwartz have cyclic structures. No fewer than four possible structures are given. See '887 at column 1, line 63-column 2, line 31.

What is now believed actually to be provided by the fatty ester-N-alkylglucamine process of Schwartz are compositions comprising mixtures of formula (1) compounds together with appreciable proportions (e.g., about 25%, often much more) of several other components, especially cyclic glucamide by-products (including but not limited to the structures proposed by Zech) or related derivatives such as esteramides wherein as compared with formula (I) at least one -OH moiety is esterified.

Moreover, a reinvestigation of Schwartz suggests that there are other significant unsolved problems in the process, including a tendency to form trace materials imparting very unsatisfactory color and/or odor to the product.

More recently, the work of Schwartz notwithstanding, Hildreth has asserted that compounds of formula (I) are new. See Biochem. J., 1982, Vol. 207, pages 363-366. In any event, these compositions are given a new name: "N-D-gluco-N-methylalkanamide detergents", and the acronym "MEGA". Hildreth provides a solvent-assisted process for making the compounds differing seminally from Schwartz in that it returns to the use of a fatty acid reactant, instead of fatty ester. Moreover, Hildreth relies on pyridine/ethyl chloroformate as the solvent/activator. This process is specifically illustrated for octanoyl-N-methylglucamide ("OMEGA"), nonanoyl-N-methylglucamide ("MEGA-9") and decanoyl-N-methylglucamide ("MEGA-10"). The process is said to be cheap and high-yield. One must of course assume that "cheap" is relative and is meant in the sense of specialized biochemical applications of interest to the author: in terms of large-scale detergent manufacture, the use of pyridine and ethyl chloroformate would hardly be viewed as consistent with an economic or environmentally attractive process. Therefore, the Hildreth process is not further considered herein.

Hildreth and other workers have purified certain formula (I) compounds, e.g., by recrystallization, and have described the properties of some of the structure (I) compounds. Recrystallization is, of course, a costly and potentially hazardous (flammable solvents) step in itself, and large-scale detergent manufacture would be more economical and safer without it.

According to Schwartz supra, the products of the Schwartz process can be used for cleaning hard surfaces. According to Thomas Hedley & Co. Ltd. (now Procter & Gamble), British Patent 809,060 published Feb. 18, 1959, formula (I) compounds are useful as a surfactant for laundry detergents such as those having granular form. Hildreth (supra) mentions use of compounds of formula (I) in the biochemistry field as a detergent agent for solubilizing plasma membranes and EP-A 285,768, published Dec. 10, 1988 describes application of formula (I) compounds as a thickener. Thus, these compounds, or compositions containing them, can be highly desirable surfactants.

Yet another process for making compositions comprising formula (I) compounds is included in the above-identified disclosure of improved thickeners. See EP-A 285,768. See also H. Kelkenberg, Tenside Surfactants Detergents 25 (1988) 8-13, inter alia for additional disclosures of processes for making N-alkylglucamines which, along with the above-identified art-disclosed N-alkylglucamine processes can be combined with the instant process for an overall conversion of glucose and fatty materials to useful surfactant compositions.

The relevant disclosures of EP-A 285,768 include a brief statement to the effect that "it is known that the preparation of chemical compounds of formula (I) is done by reacting fatty acids or fatty acid esters in a melt with polyhydroxy alkylamines which can be N-substituted, optionally in the presence of alkaline catalysts". The above-referenced art strongly suggests that this statement is a gross simplification or is inaccurate. EP-A 285,768 does not cite any references in support of the quoted statement, nor has any reference other than EP-A 285,768 been found which actually does disclose any catalytic condensation of N-alkylglucamines with fatty esters or fatty triglycerides.

The European Patent Application contains the following Example entitled "Preparation of N-methyl-coconut fatty acid glucamide" in which "Na methylate" is understood to be synonymous with "sodium methoxide" and which has been translated from the German:

In a stirred flask 669 g (3.0 mol) of coconut fatty acid methyl ester and 585 g (3.0 mol) of N-methyl glucamine with the addition of 3.3 g Na methylate were gradually heated to 135° C. The methanol formed during the reaction was condensed under increasing vacuum at 100 to 15 mbar in a cooled collector. After the methanol evolution ended the reaction mixture was dissolved in 1.5 l of warm isopropanol, filtered and crystallized. After filtration and drying 882 g (=76% of theoretical) of waxy N-methyl coconut fatty acid glucamide was obtained. Softening point=80° to 84° C.; Base number: 4 mg. KOH/g.

EP-A 285,768 continues with the following:

"In a similar manner the following fatty acid glucamides were prepared:

| | Yield % | Softening Point (°C.) | Base No. (mg. KOH/g) |
|---|---|---|---|
| N-methyl lauric acid glucamide | 76 | 94-96 | 6 |
| N-methyl myristic acid glucamide | 75 | 98-100 | 3 |
| N-methyl palmitic acid glucamide | 75 | 103-105 | 5 |
| N-methyl stearic acid glucamide | 84 | 96-98 | 6" |

To summarize some important points of what can be gleaned from the art, the aforementioned Schwartz patent teaches that the problem of making formula (I) compounds from fatty esters or triglycerides and an N-alkylglucamine is solved by selecting fatty ester (instead of fatty acid) as the fatty reactant, and by doing simple uncatalyzed condensations. Later literature, such as Hildreth, changes direction back to a fatty acid-type synthesis, but does not document either that the teaching of the Schwartz patent is in error or how, short of making highly pure formula (I) compounds, to make such surfactants to detergent formulator's specifications. On the other hand, there has been one disclosure, in a totally different technical field, of sodium methoxide-catalyzed formula (I) compound synthesis. As noted, the procedure involves gradual temperature staging up to 135° C. and recrystallizing the product.

SUMMARY OF THE INVENTION

The present invention encompasses a process for preparing polyhydroxy fatty acid amides, comprising: reacting a fatty acid ester and an N-alkyl polyhydroxy amine in one or more hydroxy solvents in the presence of a base catalyst. Preferred base catalysts herein are the alkoxide catalysts. Preferred hydroxy solvents are the $C_1-C_4$ alcohols, especially methanol.

In a typical mode, the process herein is carried out at a temperature of from about 25° C. to about 130° C. In most instances, a weight ratio of ester:N-alkyl polyhydroxy amine of at least about 1:1 is typically used.

The present process is especially useful when said N-alkyl polyhydroxy amine is of the formula $N(R^1)CH_2(CH_2OH)_4CH_2OH$. The preferred type of fatty acid ester used in the process is a $C_{12}-C_{20}$ fatty acid methyl ester.

A highly preferred process for preparing detersive surfactants is one wherein the N-alkyl polyhydroxy amine is N-methyl glucamine; the fatty acid ester is a $C_{12}-C_{20}$ methyl ester, or mixture thereof; the solvent is methanol; and the catalyst is sodium methoxide.

The invention also encompasses a polyhydroxy fatty acid amide prepared according to the above-disclosed processes having the formula $R^2C(O)N(R^1)CH_2(CH_2OH)_4CH_2OH$, wherein $R^2$ is $C_{11}-C_{19}$ alkyl, alkenyl or mixtures thereof, and $R_1$ is $C_1-C_4$ alkyl or hydroxyalkyl, said polyhydroxy fatty acid amide being prepared in purified form, said purified form comprising less than about 2%, preferably less than about 1.0%, of by-products such as ester amide, and less than about 1%, preferably less than about 0.1% by weight cyclic polyhydroxy material. Highly preferred products made by this process using N-methyl glucamine and $C_{12}-C_{14}$ methyl esters are secured in solid form by evaporation of the methanol solvent.

All percentages, ratios and proportions herein are by weight, unless otherwise specified.

DETAILED DESCRIPTION OF THE INVENTION

The amide-forming reaction herein can be illustrated by the formation of lauroyl N-methyl glucamide, as follows.

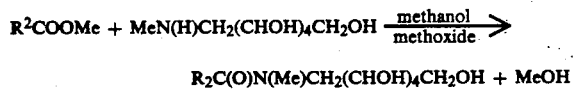

wherein $R_2$ is $C_{11}H_{23}$ alkyl.

More generally, the process herein can be used to prepare polyhydroxy fatty acid amide surfactants of the formula:

$$R^2-\underset{\underset{N}{|}}{\overset{\overset{O}{\|}}{C}}-Z \qquad (I)$$
$$\phantom{R^2-C-}R^1$$

wherein: $R^1$ is H, $C_1-C_4$ hydrocarbyl, 2-hydroxy ethyl, 2-hydroxy propyl, or a mixture thereof, preferably $C_1-C_4$ alkyl, more preferably $C_1$ or $C_2$ alkyl, most preferably $C_1$ alkyl (i.e., methyl); and $R^2$ is a $C_5-C_{31}$ hydrocarbyl moiety, preferably straight chain $C_7-C_{19}$ alkyl or alkenyl, more preferably straight chain $C_9-C_{17}$ alkyl or alkenyl, most preferably straight chain $C_{11}-C_{19}$ alkyl or alkenyl, or mixture thereof; and Z is a polyhydroxyhydrocarbyl moiety having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of $-CH_2-(CHOH)_n-CH_2OH$, $-CH(CH_2OH)-(CHOH)_{n-1}-CH_2OH$, $-CH_2-(CHOH)_2(CHOR')(CHOH)-CH_2OH$, where n is an integer from 3 to 5, inclusive, and R' is H or a cyclic mono- or poly- saccharide, and alkoxylated derivatives thereof. Most preferred are glycityls wherein n is 4, particularly $-CH_2-(CHOH)_4-CH_2OH$.

In Formula (I), $R^1$ can be, for example, N-methyl, N-ethyl, N-propyl, N-isopropyl, N-butyl, N-isobutyl, N-2-hydroxy ethyl, or N-2-hydroxy propyl.

$R^2-CO-N<$ can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The following reactants, catalysts and solvents can conveniently be used herein, and are listed only by way of exemplification and not by way of limitation.

Reactants—Various fatty esters can be used herein, including mono-, di- and tri-esters (i.e., triglycerides). Methyl esters, ethyl esters, and the like are all quite suitable. The polyhydroxyamine reactants include N-alkyl and N-hydroxyalkyl polyhydroxyamines with the N-substituent group such as $CH_3-$, $C_2H_5-$, $C_3H_7-$, $HOCH_2CH_2-$, and the like. (Polyhydroxyamines are often prepared by reaction sequences, one or more steps of which involve hydrogenation in the presence of metallic catalysts such as nickel. It is preferred that the polyhydroxyamines used herein not be contaminated by the presence of residual amounts of such catalysts, although a few parts per million [e.g., 10-20 ppm] can be present.) Mixtures of the ester and mixtures of the polyhydroxyamine reactants can also be used.

Catalysts—The catalysts used herein are basic materials such as the alkoxides (preferred), hydroxides (less preferred due to possible hydrolysis reactions, carbonates, and the like. Preferred alkoxide catalysts include the alkali metal $C_1-C_4$ alkoxides such as sodium methoxide, potassium ethoxide, and the like. The catalysts can be prepared separately from the reaction mixture, or can be generated in situ using an alkali metal such as sodium. For in situ generation, e.g., sodium metal in the methanol solvent, it is preferred that the other reactants not be present until catalyst generation is complete. The catalyst typically is used at 0.1-10, preferably 0.5-5, most preferably 1-3 mole percent of the ester reactant. Mixtures of catalysts can also be used.

Solvents—The hydroxy solvents herein include methanol, ethanol, propanol, iso-propanol, the butanols, glycerol, 1,2-propylene glycol, 1,3-propylene glycol, and the like. Methanol is a preferred alcohol solvent and 1,2-propylene glycol is a preferred diol solvent. Mixtures of solvents can also be used.

General Reaction Conditions—It is an objective herein to prepare the desired products while minimizing the formation of cyclized by-products, ester amides and color bodies. Reaction temperatures below about 135° C., typically in the range of from about 40° C. to about 100° C., preferably 50° C. to 80° C., are used to achieve this objective, especially in batch processes where reaction times are typically on the order of about 15–30 minutes, or even up to an hour. Somewhat higher temperatures can be tolerated in continuous processes, where residence times can be shorter.

The following examples are intended to illustrate the practice of the process herein, but are not intended to be limiting thereof. It is pointed out that the concentration ranges of the reactants and solvent in Example I provide what can be termed a "70% concentrated" (with respect to reactants) reaction mixture. This 70% concentrated mixture provides excellent results, in that high yields of the desired polyhydroxy fatty acid amide product are secured rapidly. Indeed, indications are that the reaction is substantially complete within one hour, or less. The consistency of the reaction mixture at the 70% concentration level provides ease of handling. However, even better results are secured at the 80% and 90% concentration levels, in that chromotography data indicate that even less of the undesired cyclized by-products are formed at these higher concentrations. However, at the higher concentrations the reaction systems are somewhat more difficult to work with, and require more efficient stirring (due to their thickness), and the like, at least in the early stages of the reaction. However, once the reaction proceeds to any appreciable extent, the viscosity of the reaction system decreases and ease of mixing increases.

EXAMPLE I

A reaction mixture consisting of 84.87 g. fatty acid methyl ester (source: Procter & Gamble methyl ester CE1270), 75 g. N-methyl-D-glucamine (source: Aldrich Chemical Company M4700-0), 1.04 g. sodium methoxide (source: Aldrich Chemical Company 16,499-2) and 68.51 g. methyl alcohol (30% by wt. of reaction mixture) is used. The reaction vessel comprises a standard reflux set-up fitted with a drying tube, condenser and stir bar. In this procedure, the N-methyl glucamine is combined with methanol with stirring under argon and heating is begun with good mixing (stir bar; reflux). After 15–20 minutes, when the solution has reached the desired temperature, the ester and sodium methoxide catalyst are added. Samples are taken periodically to monitor the course of the reaction, but it is noted that the solution is completely clear by 63.5 minutes. It is judged that the reaction is, in fact, nearly complete at that point. The reaction mixture is maintained at reflux for 4 hours. The recovered reaction mixture weighs 156.16 grams. After vacuum drying, an overall yield of 106.92 grams of granular purified product is recovered, which can easily be ground into smaller particles. However, percentage yields are not calculated on this basis, inasmuch as regular sampling throughout the course of the reaction makes an overall percentage yield value meaningless.

EXAMPLE II

An overall process at the 80% reactant concentration level for the amide synthesis is as follows.

A reaction mixture consisting of 84.87 g. fatty acid methyl ester (source: Procter & Gamble methyl ester CE1270), 75 g. N-methyl-D-glucamine, 1.04 g. sodium methoxide and a total of 39.96 g. methyl alcohol (ca. 20% by wt. of reaction mixture) is used. The reaction vessel comprises a standard reflux set-up fitted with a drying tube, condenser and mechanical stirring blade. The N-methyl glucamine/methanol is heated with stirring under argon (reflux). After the solution has reached the desired temperature, the ester and sodium methoxide catalyst are added. The reaction mixture is maintained at reflux for 6 hours. The reaction is essentially complete in 1.5 hours. After removal of the methanol, the recovered product weighs 105.57 grams. Chromatography indicates the presence of only traces of undesired ester-amide by-products, and no detectable cyclized by-product.

EXAMPLE III

The process of Example II is repeated at the 90% reactant level for the polyhydroxy fatty acid amide synthesis step. Levels of undesirable by-products are extremely low, and reaction is essentially complete at 30 minutes.

EXAMPLE IV

The process of Example I is repeated in ethanol (99%), and 1,2-propylene glycol (essentially dry), respectively, with good product formation.

While the foregoing disclosure generally relates to a solvent-assisted method for preparing glucamine-derived surfactants, it is to be understood that variations are available which do not depart from the spirit and scope of this invention. Thus, sugars, especially reducing sugars such as fructose, galactose, mannose, maltose and lactose, as well as sugar sources such as high dextrose corn syrup, high fructose corn syrup and high maltose corn syrup, and the like, can be used to prepare the polyhydroxyamine material (i.e., to replace glucamine) of the reaction. Likewise, a wide variety of fats and oils (triglycerides) can be used herein in place of the fatty esters exemplified above. For example, fats and oils such as soybean oil, cottonseed oil, sunflower oil, tallow, lard, safflower oil, corn oil, canola oil, peanut oil, fish oil, rapeseed oil, and the like, or hardened (hydrogenated) forms thereof, can be used as the source of triglyceride esters for use in the present process. The process herein is particularly useful when preparing the longer-chain (e.g., $C_{18}$) and unsaturated fatty acid polyhydroxy amides, since the relatively mild reaction temperatures and conditions herein afford the desired products with minimal by-product formation. It will be appreciated that the manufacture of detersive surfactants from such renewable resources is an important advantage of the present process.

It will be appreciated by the skilled chemist that the reaction herein can result in the formation of alcohols and/or glycols. Under some circumstances, this reactant-derived alcohol or glycol can serve a solvent function in the process.

The following is not intended to limit the invention herein, but is simply to further illustrate additional aspects of the technology which may be considered by the formulator, for example, in the manufacture of a wide variety of detergent compositions using the polyhydroxy fatty acid amides.

It will be readily appreciated that the polyhydroxy fatty acid amides are, by virtue of their amide bond, subject to some instability under highly basic or highly acidic conditions. While some decomposition can be tolerated, it is preferred that these materials not be subjected to pH's above about 11, preferably 10, nor below about 3 for unduly extended periods. Final product pH (liquids) is typically 7.0-9.0 and up to about 10.5 or 11 for solids.

During the manufacture of the polyhydroxy fatty acid amides it will typically be necessary to at least partially neutralize the base catalyst used to form the amide bond. While any acid can be used for this purpose, the detergent formulator will recognize that it is a simple and convenient matter to use an acid which provides an anion that is otherwise useful and desirable in the finished detergent composition. For example, citric acid can be used for purposes of neutralization and the resulting citrate ion (ca. 1%) be allowed to remain with a ca. 40% polyhydroxy fatty acid amide slurry and be pumped into the later manufacturing stages of the overall detergent-manufacturing process. The acid forms of materials such as oxydisuccinate, nitrilotriacetate, ethylenediaminetetraacetate, tartrate/succinate, and the like, can be used similarly.

The polyhydroxy fatty acid amides derived from coconut alkyl fatty acids (predominantly $C_{12}C_{14}$) are more soluble than their tallow alkyl (predominantly $C_{16}-C_{18}$) counterparts. Accordingly, the $C_{12}-C_{14}$ materials are somewhat easier to formulate in liquid compositions, and are more soluble in cool-water laundering baths. However, the $C_{16}-C_{18}$ materials are also quite useful, especially under circumstances where warm-to-hot wash water is used. Indeed, the $C_{16}-C_{18}$ materials may be better detersive surfactants than their $C_{12}-C_{14}$ counterparts. Accordingly, the formulator may wish to balance ease-of-manufacture vs. performance when selecting a particular polyhydroxy fatty acid amide for use in a given formulation.

It will also be appreciated that the solubility of the polyhydroxy fatty acid amides can be increased by having points of unsaturation and/or chain branching in the fatty acid moiety. Thus, materials such as the polyhydroxy fatty acid amides derived from oleic acid and iso-stearic acid are more soluble than their n-alkyl counterparts.

Likewise, the solubility of polyhydroxy fatty acid amides prepared from disaccharides, trisaccharides, etc., will ordinarily be greater than the solubility of their monosaccharide-derived counterpart materials. This higher solubility can be of particular assistance when formulating liquid compositions. Moreover, the polyhydroxy fatty acid amides wherein the polyhydroxy group is derived from maltose appear to function especially well as detergents when used in combination with conventional alkylbenzene sulfonate ("LAS") surfactants. While not intending to be limited by theory, it appears that the combination of LAS with the polyhydroxy fatty acid amides derived from the higher saccharides such as maltose causes a substantial and unexpected lowering of interfacial tension in aqueous media, thereby enhancing net detergency performance. (The manufacture of a polyhydroxy fatty acid amide derived from maltose is described hereinafter.)

As noted above, the polyhydroxy fatty acid amides can be manufactured not only from the purified sugars, but also from hydrolyzed starches, e.g., corn starch, potato starch, or any other convenient plant-derived starch which contains the mono-, di-, etc. saccharide desired by the formulator. This is of particular importance from the economic standpoint. Thus, "high glucose" corn syrup, "high maltose" corn syrup, etc. can conveniently and economically be used. De-lignified, hydrolyzed cellulose pulp can also provide a raw material source for the polyhydroxy fatty acid amides.

As noted, polyhydroxy fatty acid amides derived from the higher saccharides, such as maltose, lactose, etc., are more soluble than their glucose counterparts. Moreover, it appears that the more soluble polyhydroxy fatty acid amides can help solubilize their less soluble counterparts, to varying degrees. Accordingly, the formulator may elect to use a raw material comprising a high glucose corn syrup, for example, but to select a syrup which contains a modicum of maltose (e.g., 1% or more). The resulting mixture of polyhydroxy fatty acids will, in general, exhibit more preferred solubility properties over a broader range of temperatures and concentrations than would a "pure" glucose-derived polyhydroxy fatty acid amide. Thus, in addition to any economic advantages for using sugar mixtures rather than pure sugar reactants, the polyhydroxy fatty acid amides prepared from mixed sugars can offer very substantial advantages with respect to performance and/or ease-of-formulation. In some instances, however, some loss of grease removal performance (dishwashing) may be noted at fatty acid maltamide levels above about 25% and some loss in sudsing above about 33% (said percentages being the percentage of maltamide-derived polyhydroxy fatty acid amide vs. glucose-derived polyhydroxy fatty acid amide in the mixture). This can vary somewhat, depending on the chain length of the fatty acid moiety. Typically, then, the formulator electing to use such mixtures may find it advantageous to select polyhydroxy fatty acid amide mixtures which contain ratios of monosaccharides (e.g., glucose) to di- and higher saccharides (e.g., maltose) from about 4:1 to about 99:1.

As noted, it may be convenient for the formulator of, for example, liquid detergents to conduct such processes in 1,2-propylene glycol solvent, since the glycol solvent need not be completely removed from the reaction product prior to use in the finished detergent formulation. Likewise, the formulator of, for example, solid, typically granular, detergent compositions may find it convenient to run the process at about 30° C.-90° C. in solvents which comprise alkoxylated, especially ethoxylated, alcohols, such as the ethoxylated (EO 3-8) $C_{12}-C_{14}$ alcohols, such as those available as NEODOL 23 EO6.5 (Shell). When such ethoxylates are used, it is preferred that they not contain substantial amounts of unethoxylated alcohol and, most preferably, not contain substantial amounts of mono-ethoxylated alcohol. ("T" designation.)

Typically, the industrial scale reaction sequence for preparing the preferred acyclic polyhydroxy fatty acid amides will comprise: Step 1—preparing the N-alkyl polyhydroxy amine derivative from the desired sugar or sugar mixture by formation of an adduct of the N-alkyl amine and the sugar, followed by reaction with hydrogen in the presence of a catalyst; followed by Step 2—reacting the aforesaid polyhydroxy amine with, preferably, a fatty ester to form an amide bond. While a variety of N-alkyl polyhydroxy amines useful in Step 2 of the reaction sequence can be prepared by various art-disclosed processes, the following process is convenient and makes use of economical sugar syrup as the raw material. It is to be understood that, for best results when using such syrup raw materials, the manufacturer should select syrups that are quite light in color or, preferably, nearly colorless ("water-white").

Preparation of N-Alkyl Polyhydroxy Amine From Plant-Derived Sugar Syrup

I. Adduct Formation—The following is a standard process in which about 420 g of about 55% glucose solution (corn syrup—about 231 g glucose—about 1.28 moles) having a Gardner Color of less than 1 is reacted with about 119 g of about 50% aqueous methylamine (59.5 g of methylamine—1.92 moles) solution. The methylamine (MMA) solution is purged and shielded with $N_2$ and cooled to about 10° C., or less. The corn syrup is purged and shielded with $N_2$ at a temperature of about 10°–20° C. The corn syrup is added slowly to the MMA solution at the indicated reaction temperature as shown. The Gardner Color is measured at the indicated approximate times in minutes.

TABLE 1

| Reaction Temp. °C. | Time in Minutes | | | | | |
|---|---|---|---|---|---|---|
| | 10 | 30 | 60 | 120 | 180 | 240 |
| | Gardner Color (Approximate) | | | | | |
| 0 | 1 | 1 | 1 | 1 | 1 | 1 |
| 20 | 1 | 1 | 1 | 1 | 1 | 1 |
| 30 | 1 | 1 | 2 | 2 | 4 | 5 |
| 50 | 4 | 6 | 10 | — | — | — |

As can be seen from the above data, the Gardner Color for the adduct is much worse as the temperature is raised above about 30° C. and at about 50° C., the time that the adduct has a Gardner Color below 7 is only about 30 minutes. For longer reaction, and/or holding times, the temperature should be less than about 20° C. The Gardner Color should be less than about 7, and preferably less than about 4 for good color glucamine.

When one uses lower temperatures for forming the adduct, the time to reach substantial equilibrium concentration of the adduct is shortened by the use of higher ratios of amine to sugar. With the 1.5:1 mole ratio of amine to sugar noted, equilibrium is reached in about two hours at a reaction temperature of about 30° C. At a 1.2:1 mole ratio, under the same conditions, the time is at least about three hours. For good color, the combination of amine:sugar ratio; reaction temperature; and reaction time is selected to achieve substantially equilibrium conversion, e.g., more than about 90%, preferably more than about 95%, even more preferably more than about 99%, based upon the sugar, and a color that is less than about 7, preferably less than about 4, more preferably less than about 1, for the adduct.

Using the above process at a reaction temperature of less than about 20° C. and corn syrups with different Gardner Colors as indicated, the MMA adduct color (after substantial equilibrium is reached in at least about two hours) is as indicated.

TABLE 2

| | Gardner Color (Approximate) | | | | | | |
|---|---|---|---|---|---|---|---|
| Corn syrup | 1 | 1 | 1 | 1+ | 0 | 0 | 0+ |
| Adduct | 3 | 4/5 | 1 | 1 | 1 | 2 | 1 |

As can be seen from the above, the starting sugar material must be very near colorless in order to consistently have adduct that is acceptable. When the sugar has a Gardner Color of about 1, the adduct is sometimes acceptable and sometimes not acceptable. When the Gardner Color is above 1 the resulting adduct is unacceptable. The better the initial color of the sugar, the better is the color of the adduct.

II. Hydrogen Reaction—Adduct from the above having a Gardner Color of 1 or less is hydrogenated according to the following procedure.

About 539 g of adduct in water and about 23.1 g of United Catalyst G49B Ni catalyst are added to a one liter autoclave and purged two times with 200 psig $H_2$ at about 20° C. The $H_2$ pressure is raised to about 1400 psi and the temperature is raised to about 50° C. The pressure is then raised to about 1600 psig and the temperature is held at about 50°–55° C. for about three hours. The product is about 95% hydrogenated at this point. The temperature is then raised to about 85° C. for about 30 minutes and the reaction mixture is decanted and the catalyst is filtered out. The product, after removal of water and MMA by evaporation, is about 95% N-methyl glucamine, a white powder.

The above procedure is repeated with about 23.1 g of Raney Ni catalyst with the following changes. The catalyst is washed three times and the reactor, with the catalyst in the reactor, is purged twice with 200 psig $H_2$ and the reactor is pressurized with $H_2$ at 1600 psig for two hours, the pressure is released at one hour and the reactor is repressurized to 1600 psig. The adduct is then pumped into the reactor which is at 200 psig and 20° C., and the reactor is purged with 200 psig $H_2$, etc., as above.

The resulting product in each case is greater than about 95% N-methyl glucamine; has less than about 10 ppm Ni based upon the glucamine; and has a solution color of less than about Gardner 2.

The crude N-methyl glucamine is color stable to about 140° C. for a short time.

It is important to have good adduct that has low sugar content (less than about 5%, preferably less than about 1%) and a good color (less than about 7, preferably less than about 4 Gardner, more preferably less than about 1).

In another reaction, adduct is prepared starting with about 159 g of about 50% methylamine in water, which is purged and shielded with $N_2$ at about 10°–20° C. About 330 g of about 70% corn syrup (near water-white) is degassed with $N_2$ at about 50° C. and is added slowly to the methylamine solution at a temperature of less than about 20° C. The solution is mixed for about 30 minutes to give about 95% adduct that is a very light yellow solution.

About 190 g of adduct in water and about 9 g of United Catalyst G49B Ni catalyst are added to a 200 ml autoclave and purged three times with $H_2$ at about 20° C. The $H_2$ pressure is raised to about 200 psi and the temperature is raised to about 50° C. The pressure is raised to 250 psi and the temperature is held at about 50°–55° C. for about three hours. The product, which is about 95% hydrogenated at this point, is then raised to a temperature of about 85° C. for about 30 minutes and the product, after removal of water and evaporation, is about 95% N-methyl glucamine, a white powder.

It is also important to minimize contact between adduct and catalyst when the $H_2$ pressure is less than about 1000 psig to minimize Ni content in the glucamine. The nickel content in the N-methyl glucamine in this reaction is about 100 ppm as compared to the less than 10 ppm in the previous reaction.

The following reactions with $H_2$ are run for direct comparison of reaction temperature effects.

A 200 ml autoclave reactor is used following typical procedures similar to those set forth above to make adduct and to run the hydrogen reaction at various temperatures.

Adduct for use in making glucamine is prepared by combining about 420 g of about 55% glucose (corn syrup) solution (231 g glucose; 1.28 moles) (the solution is made using 99DE corn syrup from CarGill, the solution having a color less than Gardner 1) and about 119 g of 50% methylamine (59.5 g MMA; 1.92 moles) (from Air Products).

The reaction procedure is as follows:

1. Add about 119 g of the 50% methylamine solution to a $N_2$ purged reactor, shield with $N_2$ and cool down to less than about 10° C.
2. Degas and/or purge the 55% corn syrup solution at 10°-20° C. with $N_2$ to remove oxygen in the solution.
3. Slowly add the corn syrup solution to the methylamine solution and keep the temperature less than about 20° C.
4. Once all corn syrup solution is added in, agitate for about 1-2 hours.

The adduct is used for the hydrogen reaction right after making, or is stored at low temperature to prevent further degradation.

The glucamine adduct hydrogen reactions are as follows:

1. Add about 134 g adduct (color less than about Gardner 1) and about 5.8 g G49B Ni to a 200 ml autoclave.
2. Purge the reaction mix with about 200 psi $H_2$ twice at about 20°-30° C.
3. Pressure with $H_2$ to about 400 psi and raise the temperature to about 50° C.
4. Raise pressure to about 500 psi, react for about 3 hours. Keep temperature at about 50°-55° C. Take Sample 1.
5. Raise temperature to about 85° C. for about 30 minutes.
6. Decant and filter out the Ni catalyst. Take Sample 2. Conditions for constant temperature reactions:
   1. Add about 134 g adduct and about 5.8 g G49B Ni to a 200 ml autoclave.
   2. Purge with about 200 psi $H_2$ twice at low temperature.
   3. Pressure with $H_2$ to about 400 psi and raise temperature to about 50° C.
   4. Raise pressure to about 500 psi, react for about 3.5 hours. Keep temperature at indicated temperature.
   5. Decant and filter out the Ni catalyst. Sample 3 is for about 50°-55° C.; Sample 4 is for about 75° C.; and Sample 5 is for about 85° C. (The reaction time for about 85° C. is about 45 minutes.)

All runs give similar purity of N-methyl glucamine (about 94%); the Gardner Colors of the runs are similar right after reaction, but only the two-stage heat treatment gives good color stability; and the 85° C. run gives marginal color immediately after reaction.

EXAMPLE V

The preparation of the tallow (hardened) fatty acid amide of N-methyl maltamine for use in detergent compositions according to this invention is as follows.

Step 1—Reactants: Maltose monohydrate (Aldrich, lot 01318KW); methylamine (40 wt % in water) (Aldrich, lot 03325TM); Raney nickel, 50% slurry (UAD 52-73D, Aldrich, lot 12921LW).

The reactants are added to glass liner (250 g maltose, 428 g methylamine solution, 100 g catalyst slurry—50 g Raney Ni) and placed in 3L rocking autoclave, which is purged with nitrogen (3×500 psig) and hydrogen (2×500 psig) and rocked under $H_2$ at room temperature over a weekend at temperatures ranging from 28° C. to 50° C. The crude reaction mixture is vacuum filtered 2× through a glass microfiber filter with a silica gel plug. The filtrate is concentrated to a viscous material. The final traces of water are azetroped off by dissolving the material in methanol and then removing the methanol/water on a rotary evaporator. Final drying is done under high vacuum. The crude product is dissolved in refluxing methanol, filtered, cooled to recrystallize, filtered and the filter cake is dried under vacuum at 35° C. This is cut #1. The filtrate is concentrated until a precipitate begins to form and is stored in a refrigerator overnight. The solid is filtered and dried under vacuum. This is cut #2. The filtrate is again concentrated to half its volume and a recrystallization is performed. Very little precipitate forms. A small quantity of ethanol is added and the solution is left in the freezer over a weekend. The solid material is filtered and dried under vacuum. The combined solids comprise N-methyl maltamine which is used in Step 2 of the overall synthesis.

Step 2—Reactants: N-methyl maltamine (from Step 1); hardened tallow methyl esters; sodium methoxide (25% in methanol); absolute methanol (solvent); mole ratio 1:1 amine:ester; initial catalyst level 10 mole % (w/r maltamine), raised to 20 mole %; solvent level 50% (wt.).

In a sealed bottle, 20.36 g of the tallow methyl ester is heated to its melting point (water bath) and loaded into a 250 ml 3-neck round-bottom flask with mechanical stirring. The flask is heated to ca. 70° C. to prevent the ester from solidifying. Separately, 25.0 g of N-methyl maltamine is combined with 45.36 g of methanol, and the resulting slurry is added to the tallow ester with good mixing. 1.51 g of 25% sodium methoxide in methanol is added. After four hours the reaction mixture has not clarified, so an additional 10 mole % of catalyst (to a total of 20 mole %) is added and the reaction is allowed to continue overnight (ca. 68° C.) after which time the mixture is clear. The reaction flask is then modified for distillation. The temperature is increased to 110° C. Distillation at atmospheric pressure is continued for 60 minutes. High vacuum distillation is then begun and continued for 14 minutes, at which time the product is very thick. The product is allowed to remain in the reaction flask at 110° C. (external temperature) for 60 minutes. The product is scraped from the flask and triturated in ethyl ether over a weekend. Ether is removed on a rotary evaporator and the product is stored in an oven overnight, and ground to a powder. Any remaining N-methyl maltamine is removed from the product using silica gel. A silica gel slurry in 100% methanol is loaded into a funnel and washed several times with 100% methanol. A concentrated sample of the product (20 g in 100 ml of 100% methanol) is loaded onto the silica gel and eluted several times using vacuum and several methanol washes. The collected eluant is evaporated to dryness (rotary evaporator). Any remaining tallow ester is removed by trituration in ethyl acetate overnight, followed by filtration. The filter cake is vacuum dried overnight. The product is the tallowalkyl N-methyl maltamide.

In an alternate mode, Step 1 of the foregoing reaction sequence can be conducted using commercial corn syrup comprising glucose or mixtures of glucose and, typically, 5%, or higher, maltose. The resulting polyhydroxy fatty acid amides and mixtures can be used in any of the detergent compositions herein.

In still another mode, Step 2 of the foregoing reaction sequence can be carried out in 1,2-propylene glycol or NEODOL. At the discretion of the formulator, the propylene glycol or NEODOL need not be removed from the reaction product prior to its use to formulate detergent compositions. Again, according to the desires of the formulator, the methoxide catalyst can be neutralized by citric acid to provide sodium citrate, which can remain in the polyhydroxy fatty acid amide.

As can be seen from the foregoing, the invention herein provides a process for preparing polyhydroxy fatty acid amides, in purified substantially uncyclized form, by reacting a fatty acid ester and an N-alkyl polyhydroxy amine in one or more hydroxy or alkoxylated solvents in the presence of a base catalyst, said process being characterized by the following parameters:

(a) said base catalyst is an alkoxide catalyst;
(b) said process is carried out at a temperature of from about 25° C. to about 130° C.;
(c) said process is carried out at a weight ratio of fatty acid ester:N-alkyl polyhydroxy amine of at least about 1:1;
(d) said fatty acid ester is a $C_{12}$–$C_{20}$ a fatty acid ester; and
(e) said solvent is a $C_1$–$C_4$ alcohol, ethylene glycol, propylene glycol, glycerol, alkoxylated alcohol, or mixtures thereof.

The process herein is preferably carried out at a reaction temperature of from about 30° C. to about 90° C., preferably from about 50° C. to about 80° C., whereby cyclization reactions are substantially avoided. The process can employ N-alkyl polyhydroxy amines derived from sugars available from plant sources, especially glucose, maltose or mixtures thereof.

The invention thus provides novel compounds of the type

wherein $R^2$ is $C_{11}$–$C_{13}$ (coconut) and $C_{15}$–$C_{17}$ (tallow) alkyl or alkenyl, $R^1$ is $C_1$–$C_3$ alkyl, and Z is substantially linear and is derived from maltose.

Importantly, the invention also provides mixtures of compounds of the formula

wherein $R^2$ is $C_{11}$–$C_{17}$ alkyl or alkenyl, $R_1$ is $C_1$–$C_3$ alkyl and Z is substantially linear and is derived from mixtures of mono-, di-and, optionally, higher saccharides available from plant sources, said saccharide mixtures containing at least about 1% by weight of maltose. Such mixtures are preferably derived from plant sources of mixed sugars, said mixed sugars having a Gardner Color of about 1, or less. Such mixed polyhydroxy fatty acid amides appear to function as broad-spectrum nonionic detersive surfactants, and exhibit sudsing and/or cleaning advantages in various formulations which are superior to the pure polyhydroxy fatty acid amides, individually.

For cleaning compositions where especially high sudsing is desired (e.g., dishwashing), it is preferred that less than about 5%, more preferably less than about 2%, most preferably no $C_{14}$ or higher fatty acid be present, since these can suppress sudsing. Accordingly, preferred polyhydroxy fatty acid amide compounds and mixtures prepared by the present invention are preferably substantially free of suds-suppressing amounts of $C_{14}$ and higher fatty acids. If some fatty acid is unavoidably present, commercially-available amine oxide and/or sulfobetaine (aka "sultaine") surfactants can be used with the polyhydroxy fatty acid amides to at least partially overcome some of the negative sudsing effects. Alternatively, the polyhydroxy fatty acid amide can be prepared using fatty acid esters primarily of chain lengths lower than $C_{14}$, especially $C_{12}$ fatty methyl esters.

The polyhydroxy fatty acid amides provided herein are useful in both solid and liquid detergent compositions, which can also contain known detersive surfactants, enzymes, builders, soil release polymers and other detersive adjuncts quite well-known to the skilled artisan. The formulator wishing to add anionic optical brighteners to liquid detergents containing relatively high concentrations (e.g., 10% and greater) of anionic or polyanionic substituents such as the polycarboxylate builders may find it useful to pre-mix the brightener with water and the polyhydroxy fatty acid amide, and then to add the pre-mix to the final composition.

It will be appreciated by those skilled in the chemical arts that the preparation of the polyhydroxy fatty acid amides herein using the di- and higher saccharides such as maltose will result in the formation of polyhydroxy fatty acid amides wherein linear substituent Z is "capped" by a polyhydroxy ring structure. Such materials are fully contemplated for use herein and do not depart from the spirit and scope of the invention as disclosed and claimed.

What is claimed is:

1. A process for preparing polyhydroxy fatty acid amides, in purified substantially uncyclized form, by reacting a fatty acid ester and an N-alkyl polyhydroxy amine in one or more hydroxy or alkoxylated solvents in the presence of a base catalyst, said process being characterized by the following parameters:

(a) said base catalyst is an alkoxide catalyst;
(b) said process is carried out at a temperature of from about 25° C. to about 130° C.;
(c) said process is carried out at a weight ratio of fatty acid ester:N-alkyl polyhydroxy amine of at least about 1:1,
(d) said fatty acid ester is a $C_{12}$–$C_{20}$ a fatty acid ester; and
(e) said solvent is a $C_1$–$C_4$ alcohol, ethylene glycol, propylene glycol, glycerol, alkoxylated alcohol, or mixtures thereof.

2. A process according to claim 1 which is carried out at a reaction temperature of from about 50° C. to about 80° C., whereby cyclization reactions are substantially avoided.

3. A process according to claim 1 wherein the N-alkyl polyhydroxy amine is N-methyl glucamine; the fatty acid ester is a $C_{12}$–$C_{20}$ a methyl ester, or mixture thereof; the solvent is methanol, 1,2-propylene glycol or ethoxylated alcohol; and the catalyst is sodium methoxide.

4. A process according to claim 1 wherein the N-alkyl polyhydroxy amine is derived from sugars available from plant sources.

5. A process according to claim 4 wherein the sugar is glucose, maltose or mixtures thereof.

6. A process according to claim 5 wherein the N-alkyl polyhydroxy amine is derived from a sugar mixture comprising glucose and maltose at a weight ratio of glucose:maltose of from about 4:1 to about 99:1.

* * * * *